United States Patent [19]

Summers

[11] Patent Number: 5,383,884

[45] Date of Patent: Jan. 24, 1995

[54] SPINAL DISC SURGICAL INSTRUMENT

[75] Inventor: David P. Summers, Montgomery, Tex.

[73] Assignee: American BioMed, Inc., The Woodlands, Tex.

[21] Appl. No.: 985,329

[22] Filed: Dec. 4, 1992

[51] Int. Cl.6 ............................................. A61B 17/22
[52] U.S. Cl. ..................................... 606/170; 606/180
[58] Field of Search ............... 606/170, 169, 171, 180, 606/80; 128/751; 604/22

[56] References Cited

U.S. PATENT DOCUMENTS

| | | | |
|---|---|---|---|
| 3,732,858 | 5/1973 | Banko | 606/170 |
| 4,669,469 | 6/1987 | Gifford, III et al. | 606/170 |
| 4,955,882 | 9/1990 | Hakky | 606/170 |
| 5,074,841 | 12/1991 | Ademovic et al. | 606/170 |

FOREIGN PATENT DOCUMENTS 2660851 10/1991 France ........................ 606/170

Primary Examiner—Tamara L. Graysay
Attorney, Agent, or Firm—Gunn & Kuffner

[57] ABSTRACT

The surgical instrument of the present invention includes a cannula shaft terminating in a cutting window at the distal end of the cannula shaft. The proximal end of the cannula shaft is supported by a handle having an axial bore extending therethrough. A flexible drive shaft, connected at one end to an external drive mechanism, extends through the handle and the cannula shaft. A cutting head is mounted to the distal end of the drive shaft and positioned for cooperative cutting action with the cutting window of the cannula shaft. A non-rotating idler shaft is journaled about the drive shaft. Severed tissue is removed or evacuated from the surgical site through an annular passage formed by the cannula and idler shafts.

7 Claims, 2 Drawing Sheets

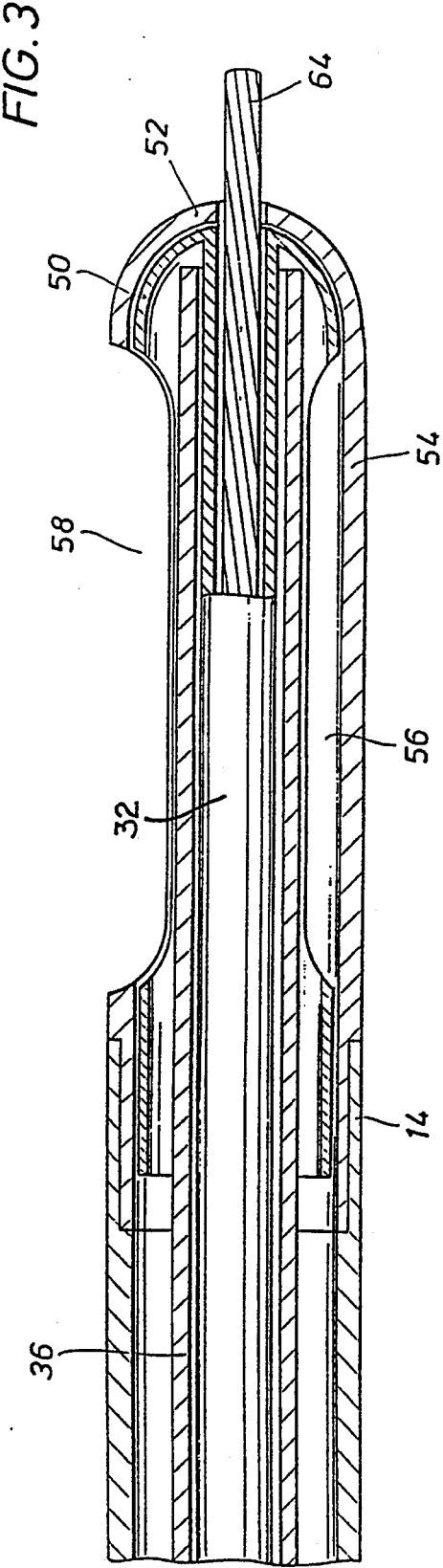
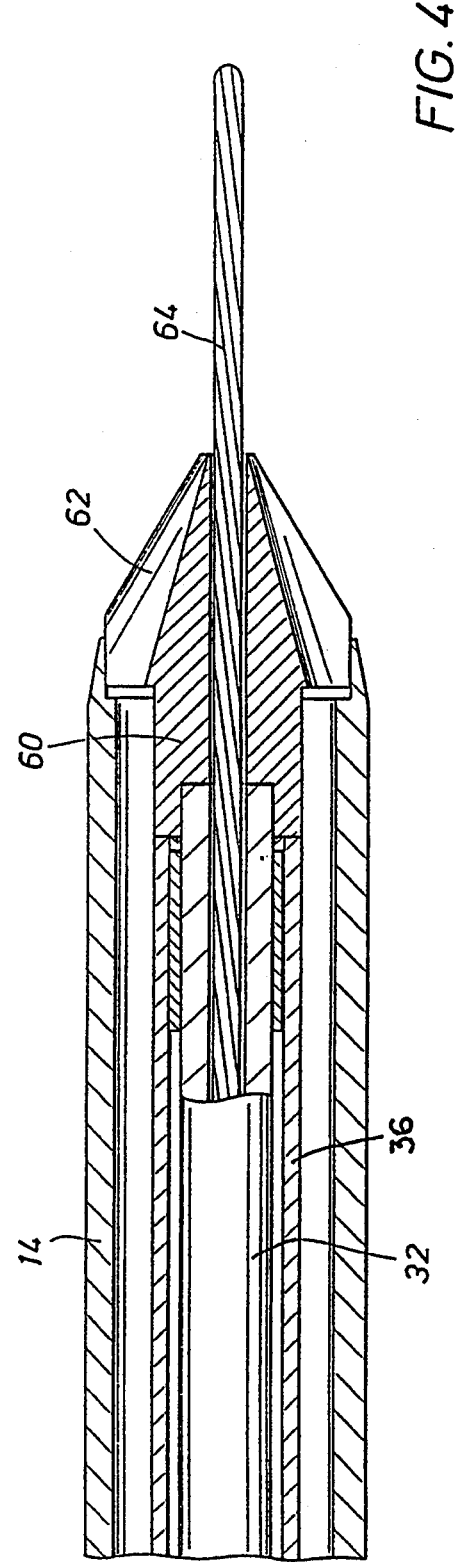

SPINAL DISC SURGICAL INSTRUMENT

BACKGROUND OF THE DISCLOSURE

The present invention relates to surgical instruments, particularly, to a surgical instrument for performing intervertebral surgery for stabilizing the spine.

A common medical condition is chronic low back pain due to spinal disc problems. Low back pain is the most frequent cause of disability in persons under age 45 years, and the third most frequent cause in the 45-64 age group. Currently, there are 2.6 million Americans temporarily disabled and another 2.6 million Americans permanently disabled by chronic low back pain. Approximately 2 percent of all workers injure their back annually.

The need to rehabilitate these patients quickly and return them to a productive life style is obvious as studies indicate the ability to ever work again decays rapidly after six months. If an injured worker has not returned to work within two years, chances are very high that he or she will never work again.

Low back pain can be avoided if relative motion between spinal vertebra can be prevented. Intervertebral stabilization is sought in a variety of treatment methods. To abate low back pain, stabilization is directed to stabilizing contiguous vertebra in the lumbar region of the spine. A common non-surgical procedures is the use of back braces. The brace is worn externally by the patient to restrict lumbar movement. The brace however is bulky and uncomfortable and limited in its effectiveness.

Laminotomy with discectomy is the standard treatment for patients with disc protrusion producing sciatica. The procedure is performed under general anesthesia. A surgical incision is made and the surgeon directly visualizes the posterior disc and nerve root. The disc extrusion or free fragments are excised and removed. However, this direct approach necessitates entry into the spinal canal, thereby putting the patient at risk for epidural bleeding, perineural fibrosis and reherniation from the site of the annular fenestration.

Low back pain is associated with the degeneration of the intervertebral disc which commonly occurs with age. Surgical stabilization seeks to rigidly join the lumbar vertebra which are separated by the degenerated disc. Ideally, the surgery effectively replaces the vertebra-disc-vertebra combination with a single rigid vertebra. That is, adjacent vertebra are fused together to form a single vertebra.

Various surgical techniques have been developed for alleviating lower back pain. One surgical approach is directed to a total disc removal through a partial hemilaminectomy. This is a major surgical procedure; it is costly and the in-hospital convalescence is long.

Another procedure, chemonucleolysis, has been developed to avoid the problems associated with major surgery. The intradiscal pressure is decreased by the percutaneous introduction of chymopapain entered into the intravertebral disc to dissolve it. Such an approach is effective in the majority of patients but does have some side effects, as some patients are hypersensitive to the drug.

Arthroscopic discectomy offers an alternative method treatment for lumbar radiculopathy due to herniated disc. Several such devices are described in U.S. Pat. No. 4,203,444; 4,598,710; 4,603,694; 4,834,729; and 5,062,845. However, none of these devices are without limitations such as the time consuming removal of very small amounts of tissue via the guillotine cutting approach, the clogging of cutters and cannula due to adherent tissue fragments and, with the use of lasers, very slow canalization of the nucleus pulposus, time consuming ablation with considerable heat and char at the operative site.

Recent clinical studies have shown that patients can benefit from minimal invasive surgery utilizing the percutaneous approach. Removal of nucleus pulposus from lumbar disc, utilizing small cannula and cannulated surgical instruments, with or without endoscopic aids, thereby reducing surgical trauma, can result in immediate relief of symptoms, low morbidity and cost efficiencies.

It is therefore an object of the present invention to provide a surgical instrument for removing all or part of a intervertebrate disc employing a minimal invasive surgical technique.

It is another object of the present invention to provide a surgical instrument that eliminates all of the aforesaid problems, does not compromise future surgical procedures and offers a number of advantages including: avoidance of epidural bleeding and perineural fibrosis, elimination of reherniation through intraoperatively induced annular fenestration, preservation of spinal stability, and the establishment of a portal space for fusion.

SUMMARY OF THE INVENTION

The surgical instrument of the present invention includes a cannula shaft terminating in a cutting window at the distal end of the cannula shaft. The proximal end of the cannula shaft is mounted to a handle. A flexible drive shaft, connected at one end to an external drive mechanism, extends through the handle and the cannula shaft. A cutting head is mounted to the distal end of the drive shaft and positioned for cooperative cutting action with the cutting window at the distal end of the cannula shaft. The drive shaft extends through a non-rotating idler shaft. Severed tissue is removed or evacuated from the surgical site through an annular passage defined between the cannula and idler shaft.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 3 is a partial, sectional view showing an alternate embodiment of the distal end of the surgical instrument of the invention; and FIG. 4 is a partial, sectional view of the distal end of the surgical instrument of the invention showing a guide wire extending through the drive shaft and cutting head of the invention.

DESCRIPTION OF THE PREFERRED EMBODIMENT

Figure 1:
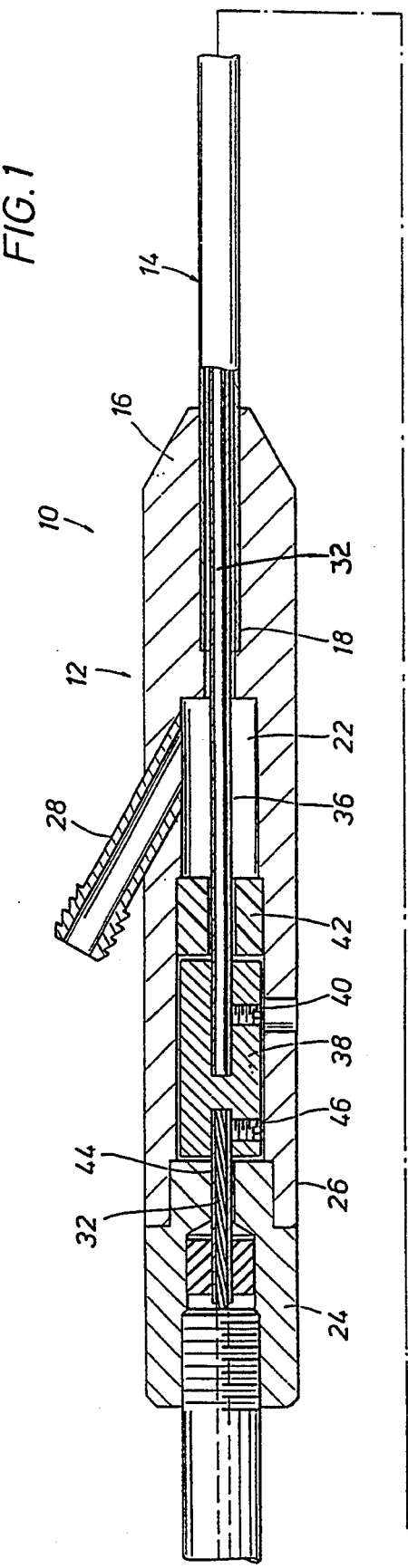
FIG. 1 is a partially broken away, sectional view of the invention.

Referring first to FIG. 1, the surgical instrument of the present invention is generally identified by the reference numeral 10. The surgical instrument 10 comprises a handle 12, a cannula shaft 14 and an external drive mechanism (not shown in the drawings). The cannula shaft 14 is a substantially rigid, hollow tubular member approximately 10 to 12 inches in length. The cannula shaft 14 is mounted to the end 16 of the handle 12. The proximal end of the cannula shaft 14 is received in a bore formed in the handle 12 which terminates at a shoulder 18. The cannula shaft 14 is press fit into the end 16 of the handle 12 so that the proximal end thereof engages the shoulder 18 formed in the handle 12.

The distal end of the cannula shaft 14 terminates in an end 20. The end 20 is slotted to form a cutting window. The end 20 may be integrally formed with the cannula shaft 14, however, for ease of manufacture, the end 20 is preferably formed as a separate component and is welded or otherwise secured to the distal end of the cannula shaft 14 as shown in greater detail in FIG. 2.

The handle 12 includes a through bore 22 axially extending through the handle 12. The proximal end of the bore 22 is closed by an end cap 24 which is press fit into the end 26 of the handle 12. An evacuation port 28 angularly extends through the body of the handle 12. The port 28 opens into the bore 22 thereby forming an evacuation passage for tissue removed at the surgical site. The port 28 provides a connection for connecting an aspirating device to the handle 12. Alternatively, the port 28 may be utilized as an injection port for delivery of medication to the surgical site.

Figure 2:
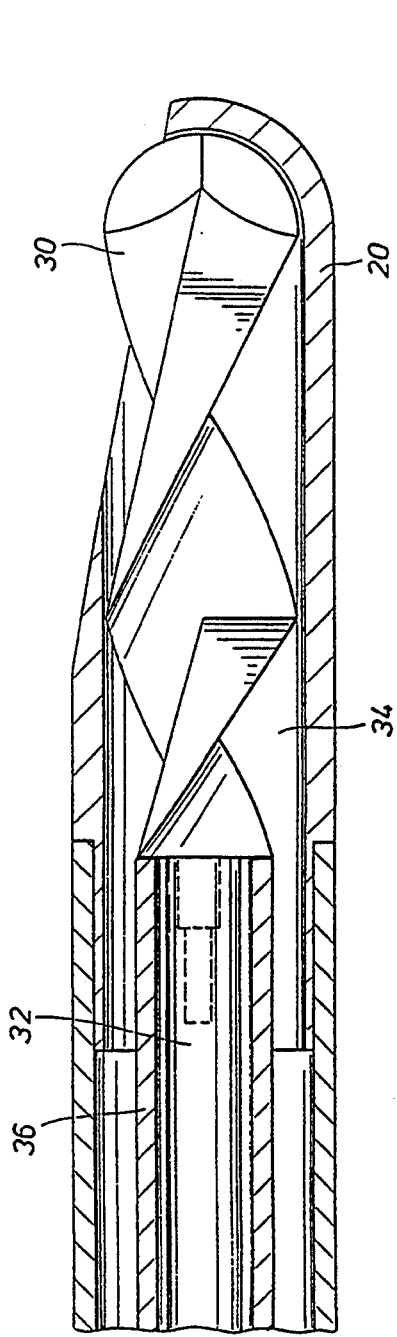
FIG. 2 is a partial, sectional view showing the distal end of the surgical instrument of the invention.

Referring now to FIG. 2, the cutting end of the surgical instrument 10 is shown in greater detail. The end 20 is slotted on one side to provide a cutting window for progressively shaving away the herniated disc. The cutter 30 is mounted on the drive shaft 32. It is welded or otherwise secured to the end of the drive shaft 32 and positioned within the end 20 of the surgical instrument 10 so that each rotation of the cutter 30 shaves off a segment of the herniated disc. The auger-like profile of the cutter 30 transports the shaved segments backward to the annulus 34. The shavings are then aspirated to a collection vessel connected to the evacuation port 28. Alternatively, the drive shaft 32 may be hollow, as shown in FIG. 4. The hollow shaft 32 extends through cutter 30 and cannula end 20, allowing a guide wire 64 to pass through the entire assembly, as best shown in FIG. 3 and FIG. 4, to facilitate passage and positioning of the cannula shaft 14 for removal of tissue at the surgical site.

Removal of the herniated disc is accomplished by shaving away bits of the disc. Each pass of the cutter 30, however, does not always sever and separate discrete portions of the disc. In addition, the suction of the aspirating device may draw tissue into the cutting chamber which will be severed by the cutter 30. Therefore, relatively long and stringy shavings or cuttings may be cut by the cutter 30. Long and stringy shavings have a tendency to wrap around a rotating drive shaft and thereby tend to block the evacuation passage. The present surgical instrument avoids this problem by incorporating an idler shaft 36 about the drive shaft 32. The idler shaft 36 does not rotate with the drive shaft 32.

However, it does tend to vibrate slightly in response to the rotating action of the drive shaft 32. The vibrating action of the idler shaft 36 agitates and dislodges shavings which might otherwise adhere to the surface of the idler shaft 36. Thus, shavings removed by the cutter 30 are quickly aspirated from the surgical site through the annulus 34 and into a collection receptacle.

Referring again to FIG. 1, it will be observed that the idler shaft 36 terminates at a coupling 38 located in the passage 22 of the handle 12. The idler shaft 36 is secured to the coupler 38 by a set screw 40 or the like. A seal 42 is journaled about the idler shaft 36 for sealing the evacuation passage. The seal 42 seals the passage 22 extending through the handle 12 so that shavings are directed through the evacuation port 28 to a collection vessel (not shown in the drawings).

The flexible drive shaft 32 extends through the end cap 24 and connects to a drive motor (not shown in the drawings). Stabilization of the flexible drive shaft 32 is provided by a stabilizer 44 which extends from the coupler 38 and into the end cap 24. The stabilizer 44 is secured to the coupler 38 by a set screw 46. The stabilizer 44 confines the flexible drive shaft 32 so that it does not whip about within the handle 12 thereby causing severe vibration of the handle 12.

Referring now to FIGS. 3 and 4, alternate embodiments of the cutting head of the surgical instrument 10 are shown. As shown in FIG. 3, the cutter 50 defines a substantially cylindrical cutting element. The cutter 50 is open at the proximal end thereof. The forwardmost or distal end of the cutter 50 is closed and defines a rounded profile substantially corresponding to the profile of the tip 52 of the cutter housing 54 which is mounted on the end of the cannula shaft 14. The cutter 50i is provided with a pair of slots 56 formed in the sidewall thereof. The slots 56 substantially correspond to the size of the cutting window 58 formed in one side of the cutter housing 54. The slots 56 are diametrically opposite each other and extend longitudinally along the sidewall of the cutter 50. The drive shaft 32 extends to the distal end of the cutter 50 and is welded or otherwise fixedly secured to the cutter 50. Likewise, the idler shaft 36 extends into the cutter 50 terminating adjacent the distal end thereof. To aid in the positioning and stabilization of the cutter 50, a guide wire 64 extends through the drive shaft 32 and the cutter 50.

The alternate embodiment of FIG. 4 depicts a cutter 60 defining a substantially conical profile. The cutter 60 includes a plurality of blades 62 spaced about the conical body of the cutter 60. The blades 62 of the cutter 60 are particularly suited for boring through or chipping away calcified matter. To aid in the positioning and stabilization of the cutter 60, a guide wire 64 extends through the drive shaft 32 and the cutter 60.

Removal of a herniated disc is accomplished with the present surgical instrument by making a small incision in the back of the patient to access the spine. The cannula shaft 14 is inserted through the incision and the cutting tip of the instrument 10 is positioned to engage the herniated disc. The cutter is rotated and by contacting the disc with the cutting tip, the surgeon may progressively shave away the herniated disc. The process is repeated until the herniated disc is completed removed.

While the foregoing is directed to the preferred embodiment of the present invention, other and further embodiments of the invention may be devised without departing from the basic scope thereof, and the scope thereof is determined by the claims which follow.

What is claimed is:

1. A surgical instrument comprising:
   (a) a substantially rigid cannula shaft, said cannula shaft including a lateral cutting port formed on the distal end thereof;
   (b) handle means supporting said cannula shaft at one end thereof, said handle means including an axial bore extending therethrough;
   (c) a drive shaft extending through said handle means and said cannula shaft, said drive shaft including cutter means mounted on the distal end thereof, said cutter means cooperating with said cutting port for severing body tissue;
   (d) an idler shaft journaled about said drive shaft and enclosing said drive shaft within said cannula shaft, said idler shaft providing a non-rotating surface for evacuation of severed tissue from the surgical site;
   (e) means connected to said drive shaft for rotating said cutter means; and
   (f) wherein said cannula shaft and said idler shaft define an annular evacuation passage therebetween for evacuation of severed tissue from the surgical site.

2. The surgical instrument of claim 1 wherein said cutter means comprises a helical cutter blade.

3. The surgical instrument of claim 1 wherein said idler shaft includes a proximal end non-rotationally secured to said handle means, and wherein the distal end of said idler shaft is coaxially supported within said cannula shaft.

4. The surgical instrument of claim 1 wherein said handle means includes an evacuation port for connection to suction means, said evacuation port communicating with said annular evacuation passage for directing severed tissue to collection means connected to said evacuation port.

5. The surgical instrument of claim 1 wherein said drive shaft is hollow, and further including a guide wire extending through said hollow drive shaft.

6. The surgical instrument of claim 1 wherein said cutter means comprises a hollow, substantially cylindrical cutting element having oppositely located cutting slots formed in the sidewall of said cutting element.

7. A surgical instrument comprising:
   (a) a substantially rigid cannula shaft;
   (b) handle means supporting said cannula shaft at one end thereof, said handle means including an axial bore extending therethrough;
   (c) a drive shaft extending through said handle means and said cannula shaft, said drive shaft including cutter means mounted on the distal end thereof, said cutter means comprising a conical shaped cutting element having a plurality of cutting blades formed thereon;
   (d) an idler shaft journaled about said drive shaft and enclosing said drive shaft within said cannula shaft, said idler shaft providing a non-rotating surface for evacuation of severed tissue from the surgical site;
   (e) means connected to said drive shaft for rotating said cutter means; and
   (f) wherein said cannula shaft and said idler shaft define an annular evacuation passage therebetween for evacuation of severed tissue from the surgical site.

* * * * *